United States Patent
Mickley

(10) Patent No.: US 6,530,914 B1
(45) Date of Patent: Mar. 11, 2003

(54) DEFLECTABLE TIP GUIDE IN GUIDE SYSTEM

(75) Inventor: Timothy J. Mickley, Elk River, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/695,525

(22) Filed: Oct. 24, 2000

(51) Int. Cl.[7] .............................................. A61M 25/01
(52) U.S. Cl. ...................................... 604/528; 604/280
(58) Field of Search .......................... 604/95.04, 528, 604/95, 280, 53; 606/45, 232

(56) References Cited

U.S. PATENT DOCUMENTS

| | | | |
|---|---|---|---|
| 4,760,131 A | 7/1988 | Sundsmo et al. | 530/356 |
| 4,790,311 A | 12/1988 | Ruiz | 128/303.1 |
| 4,896,671 A | 1/1990 | Cunningham et al. | 128/642 |
| 5,047,026 A | 9/1991 | Rydell | 606/48 |
| 5,093,877 A | 3/1992 | Aita et al. | 385/34 |
| 5,261,889 A | 11/1993 | Laine et al. | 604/164 |
| 5,287,861 A | 2/1994 | Wilk | 128/898 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,431,649 A | 7/1995 | Mulier et al. | 606/41 |

(List continued on next page.)

FOREIGN PATENT DOCUMENTS

| | | |
|---|---|---|
| DE | 296 09 350 U 1 | 10/1996 |
| DE | 195 37 084 A 1 | 4/1997 |
| WO | WO 96/35469 | 11/1996 |
| WO | WO 96/39963 | 12/1996 |

(List continued on next page.)

OTHER PUBLICATIONS

Mirhoseini et al., Abstract entitled "Transventricular Revascularization by Laser", *Lasers in Sugery and Medicine*, 2(2), 1982, 1 page.

(List continued on next page.)

*Primary Examiner*—Teresa Walberg
*Assistant Examiner*—Leonid M Fastovsky
(74) *Attorney, Agent, or Firm*—Christensen O'Connor Johnson Kindness PLLC

(57) ABSTRACT

Guide catheters which can be used in percutaneous myocardial revascularization (PMR) to deliver therapeutic catheters to difficult to reach heart chamber wall regions. Some guide catheters include distal regions which can be bent under control from the proximal region of the catheter. One steerable guide catheter has a flexible distal region, a more proximal, less flexible intermediate region, a first lumen for receiving a therapeutic catheter, and an elongate manipulation member slidably disposed in a second, blind lumen. The elongate manipulation member can be secured off-center near the distal end of the flexible distal region. The distal region can be bent by retracting the manipulation member and straightened by pushing the manipulation member. Controllably bendable guide catheters according to the present invention can be nested inside other, similar guide catheters. The invention also includes means for resisting free rotation of guide catheters relative to other adjacent catheters or tubes.

8 Claims, 5 Drawing Sheets

U.S. PATENT DOCUMENTS

| | | |
|---|---|---|
| 5,484,407 A | 1/1996 | Osypka |
| 5,522,815 A | 6/1996 | Durgin, Jr. et al. ............ 606/50 |
| 5,551,427 A | 9/1996 | Altman ........................ 128/642 |
| 5,569,462 A | 10/1996 | Martinson et al. .......... 424/424 |
| 5,591,159 A | 1/1997 | Taheri ......................... 606/15 |
| 5,593,405 A | 1/1997 | Osypka ........................ 606/15 |
| 5,607,405 A | 3/1997 | Decker et al. ............... 604/264 |
| 5,620,414 A | 4/1997 | Campbell, Jr. ................ 604/22 |
| 5,672,174 A | 9/1997 | Gough et al. .................. 606/41 |
| 5,681,308 A | 10/1997 | Edwards et al. ............... 606/41 |
| 5,683,366 A | 11/1997 | Eggers et al. ................ 604/114 |
| 5,697,882 A | 12/1997 | Eggers et al. ................ 604/114 |
| 5,700,259 A | 12/1997 | Negus et al. .................. 606/14 |
| 5,713,894 A | 2/1998 | Murphy-Chutorian et al. ........................... 606/15 |
| 5,725,521 A | 3/1998 | Mueller ......................... 606/7 |
| 5,725,523 A | 3/1998 | Mueller ........................ 606/15 |
| 5,807,318 A * | 9/1998 | St. Goar et al. .............. 604/53 |
| 5,810,836 A | 9/1998 | Hussein et al. ............. 606/108 |
| 5,843,051 A * | 12/1998 | Adams et al. ............... 604/280 |
| 5,871,495 A | 2/1999 | Mueller ....................... 606/185 |
| 5,876,373 A * | 3/1999 | Giba et al. ..................... 604/95 |
| 6,015,427 A * | 1/2000 | Mueller et al. ............. 606/232 |
| 6,027,473 A * | 2/2000 | Ponzi .......................... 604/95 |
| 6,042,581 A * | 3/2000 | Ryan et al. .................... 606/45 |
| 6,045,565 A | 4/2000 | Ellis et al. ................... 606/167 |
| 6,053,911 A | 4/2000 | Ryan et al. .................... 606/33 |
| 6,053,924 A | 4/2000 | Hussein ...................... 606/108 |
| 6,056,742 A | 5/2000 | Murphy-Chutorian et al. ........................... 606/11 |
| 6,056,743 A | 5/2000 | Ellis et al. .................... 606/15 |
| 6,126,649 A * | 10/2000 | Van'Tassel et al. ......... 604/528 |
| 6,179,809 B1 * | 1/2001 | Khairkhahan et al. ... 604/95.04 |
| 6,183,463 B1 * | 2/2001 | Webster, Jr. ................ 604/528 |

FOREIGN PATENT DOCUMENTS

| | | |
|---|---|---|
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 99/22655 | 5/1999 |
| WO | WO 99/30762 A1 | 6/1999 |
| WO | WO 00/15146 | 3/2000 |
| WO | WO 00/16704 | 3/2000 |

OTHER PUBLICATIONS

Gal et al., Abstract entitled "Analysis of Photoproducts Free Radicals and Particulate Debris Generated . . . ", *Lasers in Surgery and Medicine*, 11(2) 1991, 1 page.

Isner, J., Abstract entitled "Right Ventricular Myocardial Infarction", *JAMA*, v259, n5, Feb. 5, 1988, 12 pages.

Pickering et al., Abstract entitled "Proliferative Activity in Peripheral and Coronary Atherosclerotic Plaque . . . ", *J. Clin. Invest.*, ISSN 0021–9738, Apr. 1993, 1 page.

Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pages.

Vineberg, A., "Results of 14 Years' Experience in the Surgical Treatment of Human Coronary Artery Insufficiency", *Canad. Med. Ass. J.*, vol. 92, Feb. 13, 1965, 8 pages.

Vineberg et al., "The Ivalon Sponge Procedure for Myocardial Revascularization", *Surgery*, vol. 47, No. 2, Feb. 1960, pp. 268–289.

Vineberg et al., "Treatment of Acute Myocardial Infarction by Endocardial Resection", *Surgery*, vol. 57, No. 6, Jun. 1965, pp. 832–835.

Walter et al., "Treatment of Acute Myocardial Infarction by Transmural Blood Suply from the Ventricular Cavity", *European Surgical Research*, 3:130–138 (1971).

Khazei et al., "Myocardial Canalization", *The Annals of Thoracic Surgery*, vol. 6, No. 2, Aug. 1968, pp. 163–171.

Hershey et al., "Transmyocardial Puncture Revascularization", *Geriatrics*, Mar. 1969, pp. 101–108.

Press Release dated Oct. 21, 1996, "Doctor's Demonstrate Proof of Blood Flow Through Open TMR Channels Created with PLC Systems . . . ", 1 page.

Press/News Release dated Oct. 10, 1996, "Texas Fieart Institute Presents Study Comparing the Use of $CO2$ . . . ", 1 page.

Goldman et al., "Nonoperative Portacaval Shunt in Swine", *Investigative Radiology*, vol. 25, No. 5, May 1990, 5 pages.

Schumacher et al., "Induction of Neoangiogenesis in Ischemic Myocardium by Human Growth Factors", *Clinical Investigation and Reports*, Dec. 1, 1997, 6 pages.

Article entitled "Gene therapy improves leg circulation—next step heart?", 70th Scientific Sessions, published on or before Nov. 2, 1998, 2 pages.

Winslow, R., "Genetic Techniques Succeed in Treating Patients with Obstructed Blood Vessels", *The Wall Street Journal*, published on or before Nov. 2, 1998, 2 pages.

Kolata, G., "Gene Therapy Gives Blood a Path Around Leg Blockages, Researchers Say", *The New York Times*, Nov. 10, 1997, 2 pages.

Mack et al., "Cardiopulmonary Support and Physiology", *The Journal of Thoracic and Cardiovascular Surgery*, vol. 115, No. 1, Jan., 1998, 10 pages.

\* cited by examiner

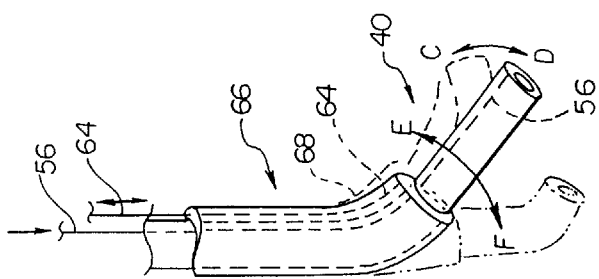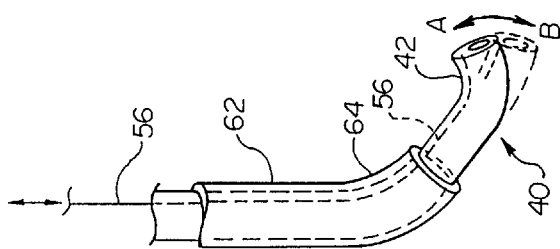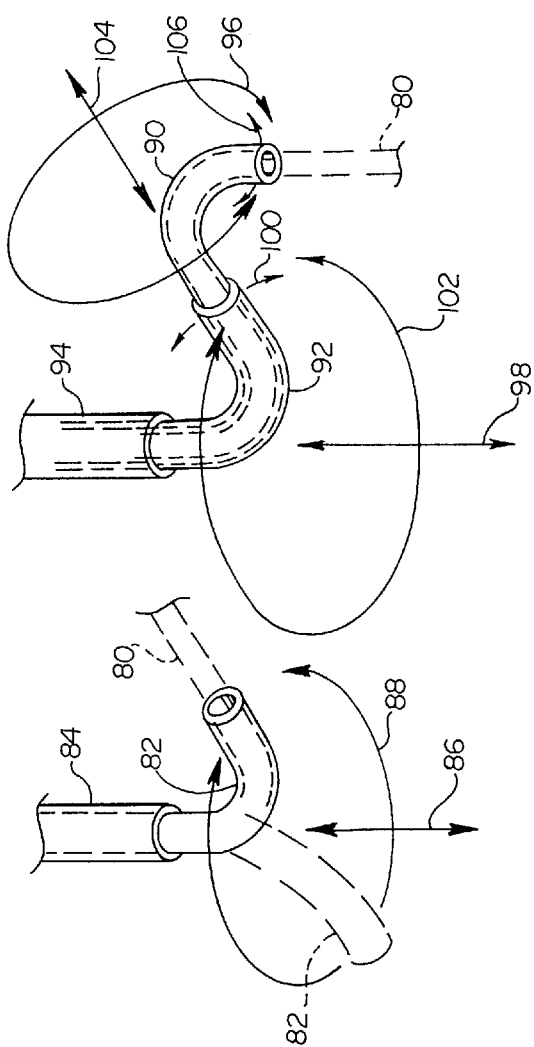

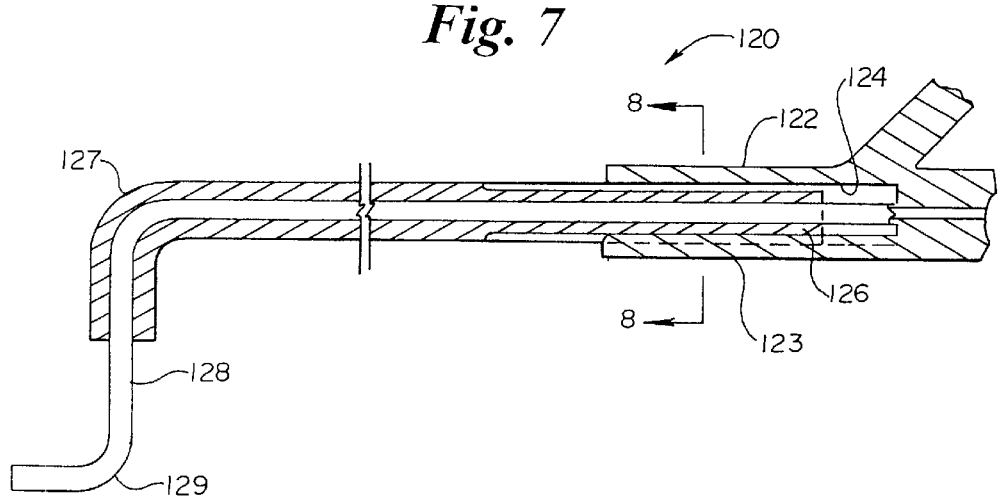

DEFLECTABLE TIP GUIDE IN GUIDE SYSTEM

FIELD OF THE INVENTION

The present invention is related generally to medical devices. More specifically, the present invention is related to catheters for performing percutaneous myocardial revascularization (PMR) which is also referred to as transmyocardial revascularization (TMR). The present invention includes guide catheters having proximally controllable distally disposed bendable regions.

BACKGROUND OF THE INVENTION

A number of techniques are available for treating cardiovascular disease such as cardiovascular by-pass surgery, coronary angioplasty, coronary atherectomy, and stent placement. These techniques are generally applied to by-pass or open lesions in coronary vessels to restore patency and increase blood flow to the heart muscle. In some patients, the number of lesions is so great, or the location so remote in the coronary vasculature, that restoring coronary artery blood flow to the heart is difficult. Transmyocardial revascularization (TMR), also known as percutaneous myocardial revascularization (PMR), has been developed as an alternative to these techniques which are directed to bypassing or removing lesions.

Heart muscle may be classified as healthy, hibernating, and "dead." Dead tissue is not dead but is scarred, no longer contracting, and no longer capable of contracting even if adequately supplied with blood. Hibernating tissue is not contracting muscle tissue but is capable of contracting, provided it is again adequately supplied with blood. PMR is performed by wounding the myocardium of the heart, often forming and leaving patent holes, and sometimes injecting angiogenic substances in the process.

PMR was inspired in part by observations that reptilian hearts are supplied in large part by blood supplied directly from within the heart chambers. In contrast, mammalian hearts are supplied by blood pumped from the heart, through the aorta, and back into the heart muscle through the coronary arteries. Positive results have been observed in some patients receiving PMR treatments. The positive results may be due in part to blood being perfused into the myocardium from the heart chambers through holes into the myocardium which remain open. The positive results are believed to be due in part to a wound healing response of the myocardium which includes formation of new blood vessels in the heart wall, which are believed to connect with the heart chamber interior and/or other coronary blood vessels. The PMR procedure can include cutting into the myocardium with therapeutic cutting tips, burning holes with therapeutic tips having laser or radio frequency current burning tips. The PMR therapeutic tip can also be used to inject angiogenic substances, such as growth factors or genes selected to cause angiogenesis.

The PMR procedure generally involves insertion of a therapeutic tip, such as sharp cutting tip, into the heart chamber or chambers selected for treatment. The cutting tip and associated inner shaft can be guided into the chamber through a guide catheter, which may have been inserted into the vasculature a long distance from the heart. After the inner shaft exits the guide catheter, the cutting tip is preferably steered to several positions for forming of several holes in a pattern across the endocardium. In order to steer the inner shaft and cutting tip, an outer shaft or tube is sometimes disposed coaxially about the inner shaft and within the guide catheter. The outer tube can have structural features at the distal end for bending to various angles to reach various locations in the heart wall. The outer tube and inner shaft can be advanced to bring the cutting tip into contact with the heart wall.

It may be desirable to revascularize regions of the endocardium that are difficult to reach using conventional guide catheters. For example, it may be important to reach areas of hibernating tissue in superior locations of the left ventricle. Conventional guide catheters may have difficulty bending sufficiently to reach some regions.

What would be desirable is an improved guide device for steering inner shaft cutting tips into position within the heart myocardium. What would be desirable is a catheter having greater reach and maneuverability in the chambers of the heart.

SUMMARY OF THE INVENTION

The present invention includes guide catheters which can be used for performing percutaneous myocardial revascularization (PMR). Guide catheters incorporating the present invention can provide distal regions that can be bent through varying angles. The distal region bending is preferably controlled at a proximal region or proximal end of the guide catheter. One controllably bendable guide catheter has a first lumen for receiving and delivering a therapeutic catheter to the guide catheter distal end and beyond. The guide catheter can also have an elongate manipulation member extending from the proximal region of the guide catheter to near the distal end of the guide catheter. The member is preferably secured to a location off-center from the central longitudinal axis of the catheter. In one embodiment, the distal end of the member is bonded to the body of the guide catheter at the distal end of a second, blind lumen near the guide catheter distal end.

The manipulation member is a pull wire in some embodiments. The manipulation member in one embodiment is a flat metallic ribbon. In some embodiments, the manipulation member is a pull wire which may be formed from metal. In one embodiment, the member is capable of both pushing on the distal region to straighten the distal region and pulling on the distal region through the off-center attachment point to impart a curve or bend to the distal region. In another embodiment, the manipulation member is sufficiently strong only in tension, with a straightening bias in the distal region used to straighten the distal region when tension is released. The guide catheter distal region is preferably formed of a more flexible material than the more proximal intermediate guide catheter region.

A controllably bendable guide catheter, according to the present invention, can be inserted through a conventional guide catheter in one PMR system. In another PMR system, the bendable guide catheter is nested within a second controllably bendable guide catheter. This can provide for great flexibility in reaching otherwise hard to reach sites in the endocardium.

Another aspect of the present invention provides for inhibiting free rotation between nested, rotating tubes such as the nested guide catheter tubes. The rotation inhibitor can include internal and external teeth on opposing external and internal opposing surfaces, respectively. The teeth can engage each other and resist rotation between the inner and outer tubes. When the applied rotational force exceeds a threshold, elastic deformation of the teeth can allow slippage between the opposed teeth and the two tubes. Providing resistance to free rotation between the tubes can lessen the rotation of the two tubes relative to one another in the case where torque has been applied to one tube, but has not been translated to rotational motion at the distal end. The applied torque may have been stored in the intermediate portion of the tube and can cause unwanted rotation of either tube at the proximal end. A ratcheting mechanism can be provided which urges the tubes to stay in position after the treating physician's hands are removed from the device.

BRIEF DESCRIPTION OF THE DRAWINGS

FIG. 3 is a fragmentary, perspective view of a steerable inner guide catheter disposed within an outer guide catheter;

FIG. 4 is a fragmentary, perspective view of a steerable inner guide catheter disposed within an outer steerable guide catheter;

FIG. 5 is a fragmentary, perspective view of a PMR therapeutic catheter disposed within a steerable guide catheter disposed within a guide catheter;

FIG. 6 is a fragmentary, perspective view of a PMR therapeutic catheter disposed within a steerable inner guide catheter disposed within an outer steerable guide catheter disposed within a guide catheter;

FIG. 7 is a longitudinal cross-sectional view of a rotatable, steerable guide catheter disposed within a rotatable guide catheter disposed within a proximal hub;

DETAILED DESCRIPTION OF THE INVENTION

Figure 1:
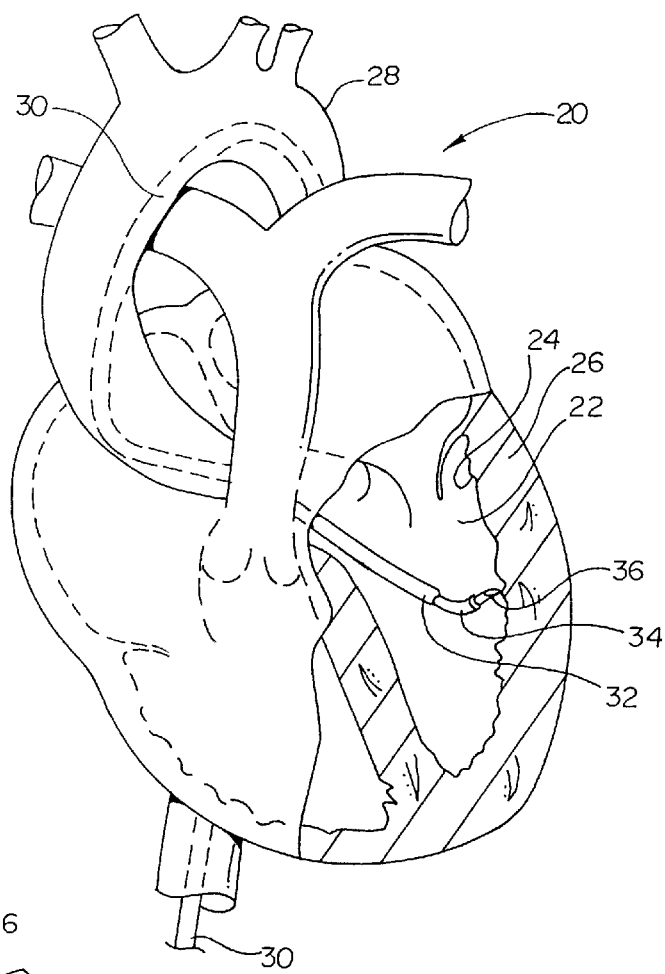
FIG. 1 is a perspective, cutaway view of a heart having a PMR therapeutic catheter disposed within a steerable or controllably bendable guide catheter disposed within a guide catheter.

FIG. 1 illustrates a human heart 20 having a left ventricle 22, an inner layer to a heart chamber wall or endocardium 24, a heart chamber wall or myocardium 26, and an aortic arch 28. Disposed through the aortic arch is a percutaneous myocardial revascularization (PMR) device 30, extending into left ventricle 22 and having an outer guide tube 32, an inner guide tube 34, and a therapeutic catheter therapeutic tip 36 near endocardium 24. As can be seen from inspection of FIG. 1, left ventricle 22 includes upper or superior regions that may require a bend in PMR device 30 in order to reach the superior regions of the myocardium. In the embodiment illustrated, inner guide catheter 34 includes a bent distal region for orienting therapeutic catheter tip 36 toward a target location in the myocardium.

Figure 2:
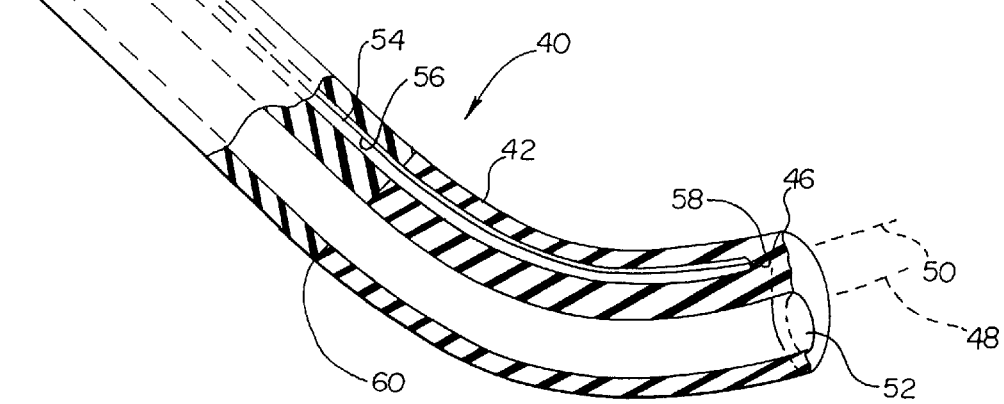
FIG. 2 is a fragmentary, perspective, cutaway view of a controllably bendable guide tube having a bendable distal region and an elongate manipulation member.

Referring now to FIG. 2, one embodiment of a steerable or bendable guide catheter 40 is illustrated in more detail. Guide catheter 40 includes a distal region 42, an intermediate region 44 disposed proximal of the distal region, and a distal end 46. A longitudinal center axis 48 is illustrated near distal end 46, as is an off-center axis 50 disposed laterally offset from center axis 48. Guide catheter 40 includes a lumen 52 for receiving a therapeutic catheter, or, in some embodiments, another guide catheter. A second lumen 54 is illustrated, having an elongate manipulation member 56 disposed within. Second lumen 54 need not extend through to distal end 46 in most embodiments. In the embodiment illustrated, elongate manipulation member 56 is secured to the body of catheter 40 at an off-center attachment point 58 which is located along off-center axis 50. By pulling on manipulation member 56 which is attached off-center to guide catheter 40, distal region 42 can be made to bend or deflect. In one embodiment, manipulation member 56 is sufficiently strong in tension to pull distal region 42 to bend the region, and sufficiently strong in compression to push distal region 42 to straighten the region. In one embodiment, manipulation member 56 is a flat wire. In one embodiment, manipulation member 56 is a pull wire strong enough in tension to bend distal region 42 but insufficiently strong in compression to straighten distal region 42, with distal region 42 being biased to a straight position and resuming that position when the tension of manipulation member 56 is released.

Guide catheter 40 distal region 42 is preferably formed of a more flexible material than intermediate region 44. In the embodiment illustrated, distal region 42 is bonded to intermediate region 44 along a plane as illustrated at 60. In one embodiment, distal region 42 and intermediate region 44 are formed of materials such as polyether ester elastomer (for example, ARNITEL®, available from DSM Engineering Plastics), a polyester elastomer (for example, HYTREL®, available from DuPont Corporation), a polyether block amide (for example, PEBAX®), or Nylon. The two regions can be bonded together using a method well known to those skilled in the art, such as adhesive application or heat bonding. In one embodiment, intermediate region 44 is formed from the same polymer as distal region 42, but having a higher durometer value.

Referring now to FIG. 3, steerable guide catheter 40 having bendable distal region 42 is shown disposed within a second guide catheter 62 having a bent distal region 64. In some embodiments, distal bent region 64 is relatively fixed in the degree of bend, and the bend may be used in part to gain entry to the left ventricle. The length of guide catheter 40 that extends from second guide catheter 62 can be varied to reach varying locations of the endocardium in the heart chambers such as the left ventricle. The distal bend of guide catheter 40 can be used to point a therapeutic catheter to various locations in the heart wall. Guide catheter distal region 42 is illustrated in a first bend position "A" and a second, straighter bend position "B". In the embodiment illustrated, movement between positions A and B is accomplished through the longitudinal movement of elongate manipulation member 56.

Referring now to FIG. 4, guide catheter 40 is shown disposed within a steerable second guide catheter 66 having a distal bend region 68. Guide catheter 40 is shown in two positions, "C" and "D", while second steerable guide catheter 62 is illustrated in two positions, "E" and "F". Second steerable guide catheter 66 controls the bend of distal region 68 through a slidable elongate manipulation member 64. As shown in FIG. 4, the combination of two independently controlled degrees of bending allows a large degree of control over where in the heart chamber a carried therapeutic catheter tip is to be delivered.

FIG. 5 illustrates a therapeutic cutting tip catheter 80 disposed within a bent, steerable guide catheter 82 slidably and rotatably disposed within an outer guide catheter 84. FIG. 5 illustrates the range of motion possible through rotation and axial movement, with rotation indicated at 88 and axial movement indicated at 86. These ranges of movement are also possible in addition to the illustrated controlled bending illustrated in FIGS. 3 and 4, but difficult to show on the same figure.

FIG. 6 illustrates yet another embodiment, illustrating therapeutic cutting tip catheter 80 slidably disposed within a first bendable guide catheter 90 which is slidably and rotatably disposed within a second bendable guide catheter 92, which is in turn slidably and rotatably disposed within a third, more conventional guide catheter 94. The range of motion of guide catheter 90 is indicated by rotation at 96, axial movement at 104, and bending at 106. Similarly, the range of motion of guide catheter 92 is indicated by rotation at 102, axial movement at 98, and bending at 100.

In one embodiment, guide catheters 90 and 92 are controlled with an elongate manipulation member similar to guide catheters 40 and 66 of FIG. 4. FIG. 6 thus illustrates how bendable, steerable guide catheters can be nested within each other to multiple levels to achieve a large range of motion. With reference to FIGS. 1, 5 and 6, it may be seen that the bendable distal region of the guide catheters can bring a large portion of the left ventricle endocardium into range of the catheter therapeutic tip, giving the ability to treat a large portion of the left ventricle myocardium.

Referring now to FIG. 7, another aspect of the present invention is illustrated. Inspection of FIGS. 4 through 6 illustrates guide tubes disposed within guide tubes. As explicitly indicated in FIG. 5 at 88 and in FIG. 6 at 96 and 102, rotation of tubes within tubes is possible. In order to provide the largest tubular lumens while providing small outer diameters, the nested guide catheters may be closely matched in size, with little wasted space in between the outside wall of an inner tube and the inside wall of an outer tube. In some embodiments, the catheters allow for more space in between the tubes, but can have one wall lying more closely to one wall than another, as the nested guide catheters are curved around tortuous vessels turns which can force the inner catheter off-center to lie more closely to one inside surface of the outer catheter.

The closeness of one or both walls of the inner and outer catheters can thus inhibit rotation of one tube relative to another tube. In particular, applied rotational force may not be completely translated into rotational movement at the far distal end of the inner catheter. This can result in some applied torque being stored as torsional energy in the inner catheter. When the treating physician releases the inner catheter proximal end after applied torque to the inner catheter, the proximal end of the inner catheter may spring back. If the outer catheter was being held and then released, the outer tube may spring in the same direction as the applied force to the inner tube. Thus, it is possible for one tube to freely rotate even in the absence of currently applied force to that tube by the treating physician.

Figure 8:
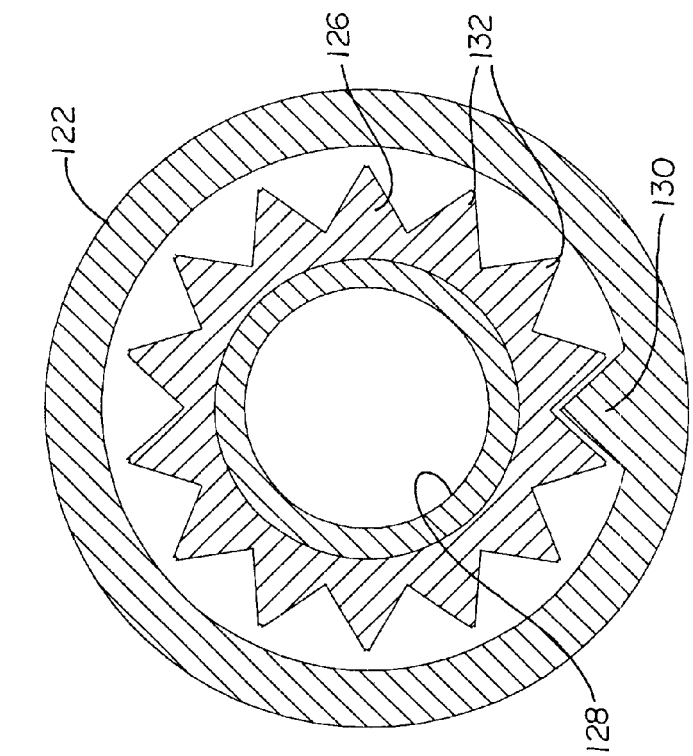
FIG. 8 is a transverse cross-sectional view of the catheter of FIG. 7 taken through place 8—8, illustrating external teeth on the rotatable, steerable guide catheter engaged with an internal tooth on the rotatable guide catheter for inhibiting free rotation between the two.

FIGS. 7 and 8 illustrate a catheter system 120 having structures for inhibiting the undesirable rotational movement of one catheter when no torque is being applied at the proximal end by the treating physician. The structures can prevent the guide catheters from undesirably rotating one within the other. Catheter system 120 includes a proximal region 123, and a proximal hub 122 having a lumen 124 therein for receiving a first guide catheter 126, which is disposed about a second guide catheter 128. In the embodiment illustrated, first guide catheter 126 has a distal region 127 having a bend and second catheter 128 also has a distal region 129 having a bend. In one embodiment, second catheter distal region 129 can be bent, with the bending being controlled from a more proximal region of the catheter. Second catheter 128 can be rotated relative to first catheter 126, and first catheter 126 can be rotated relative to enclosing hub 122.

FIG. 8 illustrates an aspect of the invention which can inhibit free rotation of first catheter 126 relative to hub 122. Hub 122 has an internal tooth 130 and first catheter 126 has several outwardly extending teeth 132 in proximal hub region 123. When first catheter 126 is rotated relative to hub 122 and/or second catheter 128 is rotated relative to first catheter 126, rotational energy may later cause first catheter 126 to rotate. To inhibit this free rotation, tooth 130 engages teeth 132 and inhibits this free rotation. When sufficient force is applied, the teeth can be forced to move over each other, allowing for rotation. In one embodiment, this movement is possible due to the elastic deformation of at least one of the pairs of opposing teeth. In one embodiment, the outer tooth is replaced by multiple teeth. The inner and outer teeth may be formed of materials such as DELRIN® (an acetal plastic available from DuPont Chemical Company), PEBAX® (polyether block amide), polyesters, polycarbonate, ABS (acrylonitrile butadiene styrene), acrylic, or ULTEM® (a polyetherimide available from General Electric Corporation).

Figure 9:
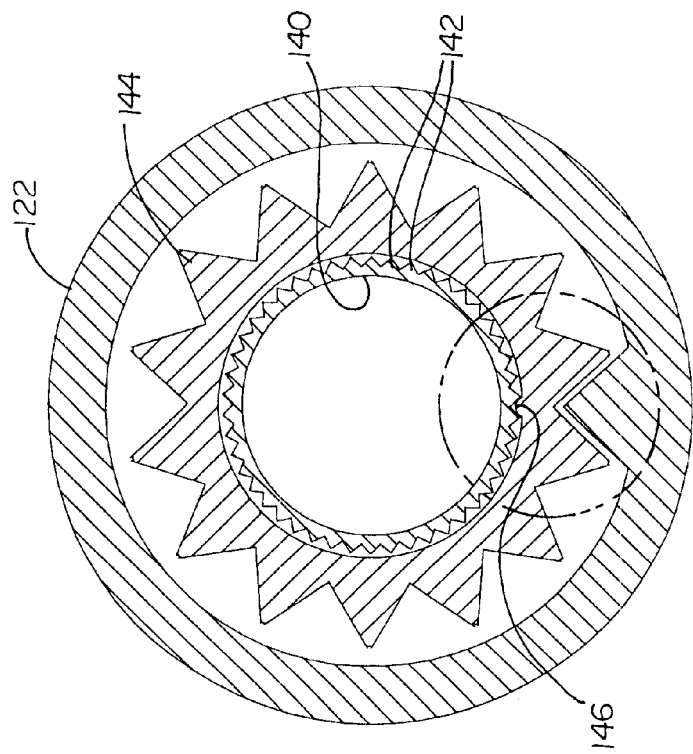
FIG. 9 is a transverse cross-sectional view somewhat similar to that of FIG. 8, wherein the steerable guide catheter has external teeth engaged with an internal tooth of the rotatable guide catheter.
Figure 10:
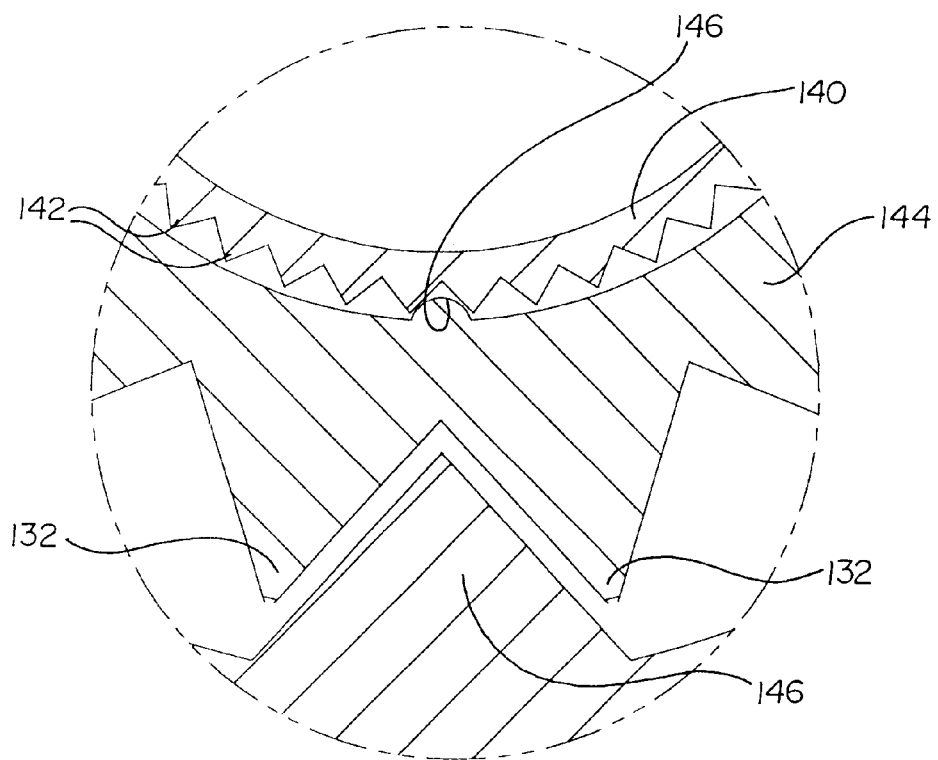
FIG. 10 is a detailed view of the inset portion of FIG. 9.

FIG. 9 illustrates another embodiment having teeth on both an inner and an outer guide catheter. An inner guide catheter 140 is disposed within an outer guide catheter 144, which is in turn disposed within hub 122. In the embodiment illustrated, inner guide catheter 140 has several outer teeth 142 which engage a single inwardly oriented tooth 146 of outer guide catheter 144. In this embodiment, the free rotation of inner catheter 140 relative to outer guide catheter 144 is inhibited. FIG. 10 illustrates outer guide catheter 144 with inwardly disposed tooth 146 in greater detail. FIGS. 8, 9, and 10 illustrate embodiments of the invention capable of resisting stored torsional energy from causing free rotation of the guide catheter when the applied torque is removed.

In use, a guide catheter according to the present invention can be advanced to a target site. In some methods, this is accomplished by first introducing a guide wire through the vasculature and into a heart chamber to be treated, such as the left ventricle. For example, a guide wire can be introduced into the femoral artery near the groin, and advanced over the aortic arch and into a chamber of the heart. A guide catheter can then be advanced over the guide wire. The first guide catheter can be followed by a second guide catheter, either over the first guide catheter or over the guide wire within the first guide catheter. The guide wire can be retracted and a therapeutic catheter advanced through the inner most guide catheter. Multiple guide catheters can thus be advanced to position.

In some applications of the present invention, a steerable guide catheter having a controllably bendable distal region is disposed within a conventional guide catheter. The conventional guide catheter can terminate distally in either a straight distal region or a curved distal region, depending on the application. In other applications, a first guide catheter having a controllably bendable distal region is disposed within a second guide catheter having a controllably bendable guide catheter. In either case, the guide catheter or catheters can be advanced into the heart chamber with the therapeutic catheter tip disposed within the inner most guide catheter.

The innermost guide catheter can be extended toward a target site of interest with the longitudinal extension and radial rotation of the catheter proximally controlled by the treating physician. The bending of the guide catheter distal region can also be controlled by the treating physician. In preferred embodiments, at least a portion of the therapeutic catheter or therapeutic tip is radiopaque to make the tip location visible under fluoroscopy. The extension, rotation, and bending can be observed under fluoroscopy, with the extension, rotation, and manipulation of bending controlled in response to the image seen under fluoroscopy. In some methods, one or two of the movements, extension, rotation, or bending, may be controlled while the other one or two movements are varied in order to cover a pattern of the heart wall. For example, the rotation may be held constant, and the bend may be varied, with the longitudinal extension being varied sufficiently to reach the heart wall. For example, the bend may be held constant, and the rotation may be varied, to cover a circular pattern over a portion of the heart wall. In use, various therapeutic tips may be delivered to the endocardium, including cutting tips, burning tips, and angiogenic substance injecting tips.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A guiding catheter system for performing myocardial revascularization comprising:
   a first guide tube having a proximal region and a first lumen therethrough, said first lumen having an inside surface;
   a second guide tube having a proximal region and a second lumen therethrough, said second guide tube being disposed at least partially in said first tube first lumen and having an outer surface opposing said first guide tube inside surface; and
   means disposed on the surfaces of the first and second guide tubes for resisting free rotation between said first and second guide tubes.

2. A guiding catheter system for performing myocardial revascularization as recited in claim 1, wherein said means for resisting free rotation includes a plurality of teeth disposed on at least one of said opposing surfaces and at least one tooth on the other of said opposing surfaces for engaging said plurality of teeth.

3. A guiding catheter system for performing myocardial revascularization as recited in claim 2, wherein said plurality of teeth is disposed on said first tube outer surface and said at least one tooth is disposed on said second tube inner surface.

4. A catheter system, comprising:
   a first catheter having an outer surface, an inner surface, and a lumen extending along the length of the first catheter;
   a second catheter having an outer surface, an inner surface, and a lumen extending along a length of the second catheter, the second catheter fitting within the lumen of the first catheter; and
   an engagement mechanism capable of elastic deformation that allows free rotation of the second catheter within the lumen of the first catheter when the rotation has a force that elastically deforms the engagement mechanism.

5. The catheter of claim 4, wherein the engagement mechanism is disposed between the inner surface of the first catheter and the outer surface of the second catheter.

6. The catheter system of claim 5, wherein the engagement mechanism comprises a ring of teeth disposed on one of the inner surface of the first catheter or the outer surface of the second catheter and at least one engaging tooth that engages the ring of teeth, the at least one engaging tooth disposed opposite the ring of teeth.

7. A catheter system, including:
   a hub having a lumen extending therethrough;
   a catheter that fits within the lumen of the hub; and
   an engagement mechanism disposed in the hub for opposing the rotation of the catheter in the hub, wherein the engagement mechanism can be elastically deformed to rotate the catheter in the hub.

8. The catheter system of claim 7, wherein the engagement mechanism comprises a number of interlocking teeth disposed on opposing surfaces of the hub and catheter, at least some of the teeth being elastically deformed out of engagement when the catheter is rotated in the hub.

* * * * *

UNITED STATES PATENT AND TRADEMARK OFFICE
CERTIFICATE OF CORRECTION

PATENT NO.    : 6,530,914 B1
DATED         : March 11, 2003
INVENTOR(S)   : T.J. Mickley It is certified that error appears in the above-identified patent and that said Letters Patent is hereby corrected as shown below:

<u>Title page,</u>
Item [57], ABSTRACT,
Lines 1-18, delete in its entirety and substitute
-- A catheter system includes a mechanism for preventing the rotation of a catheter in a hub or a catheter within a second catheter. In one embodiment, the mechanism includes teeth on opposing surfaces of the catheters and/or hub that frictionally engage. The teeth are elastically deformed to permit rotation of the catheters. --

Signed and Sealed this

Tenth Day of February, 2004

JON W. DUDAS
*Acting Director of the United States Patent and Trademark Office*